(12) United States Patent
Sasaki

(10) Patent No.: US 6,296,811 B1
(45) Date of Patent: Oct. 2, 2001

(54) FLUID DISPENSER AND DISPENSING METHODS

(75) Inventor: Glenn C. Sasaki, Santa Fe, CA (US)

(73) Assignee: Aurora BioSciences Corporation, San Diego, CA (US)

( * ) Notice: Subject to any disclaimer, the term of this patent is extended or adjusted under 35 U.S.C. 154(b) by 0 days.

(21) Appl. No.: 09/210,260

(22) Filed: Dec. 10, 1998

(51) Int. Cl.[7] ....................................................... G01N 1/14
(52) U.S. Cl. ...................... 422/100; 436/180; 73/863.32; 73/864.02; 347/68; 347/71; 310/326; 310/328
(58) Field of Search ................................. 347/68, 69, 70, 347/71, 72, 94; 422/99, 100; 310/326, 328, 369; 436/180; 73/863.32, 864.02

(56) References Cited

U.S. PATENT DOCUMENTS

| | | | |
|---|---|---|---|
| 3,683,212 | * | 8/1972 | Zoltan ............................... 310/8.3 |
| 3,832,579 | | 8/1974 | Arndt . |
| 3,946,398 | * | 3/1976 | Kyser et al. ............................. 346/1 |
| 4,032,929 | * | 6/1977 | Fischbeck et al. ................. 346/140 R |
| 4,104,646 | * | 8/1978 | Fischbeck ......................... 346/104 R |
| 4,233,610 | | 11/1980 | Fischbeck et al. . |
| 4,272,200 | * | 6/1981 | Hehl ..................................... 400/124 |
| 4,308,546 | * | 12/1981 | Halasz .............................. 346/104 R |
| 4,395,719 | * | 7/1983 | Majewski et al. ................ 346/140 R |
| 4,418,354 | | 11/1983 | Perduijn . |
| 4,424,520 | * | 1/1984 | Matsuda et al. .................. 346/140 R |
| 4,520,374 | * | 5/1985 | Koto ................................. 346/140 R |
| 4,523,199 | * | 6/1985 | Ott ........................................ 346/1.1 |
| 4,528,579 | | 7/1985 | Brescia . |
| 4,550,325 | * | 10/1985 | Viola ................................ 346/104 R |
| 4,566,017 | * | 1/1986 | Nilsson ............................ 346/104 R |
| 4,605,939 | * | 8/1986 | Hubbard et al. ................. 346/140 R |
| 4,672,398 | * | 6/1987 | Kuwabara et al. .............. 346/140 R |
| 4,752,788 | | 6/1988 | Yasuhara et al. . |
| 4,877,745 | | 10/1989 | Hayes et al. . |
| 4,879,568 | | 11/1989 | Bartky et al. . |
| 4,992,808 | | 2/1991 | Bartky et al. . |
| 5,432,540 | | 7/1995 | Hiraishi . |
| 5,627,576 | * | 5/1997 | Inui et al. .............................. 347/48 |
| 6,232,129 | * | 5/2001 | Wiktor ................................. 436/180 |

FOREIGN PATENT DOCUMENTS

| | | |
|---|---|---|
| 0 810 438 A2 | 12/1997 | (EP) . |
| 55065569 | 5/1980 | (JP) . |
| 57029463 | 2/1982 | (JP) . |
| 57144767 | 9/1982 | (JP) . |
| WO 97/44134 | 11/1997 | (WO) . |

* cited by examiner

Primary Examiner—Jill Warden
Assistant Examiner—Kathryn Bex
(74) Attorney, Agent, or Firm—Knobbe, Martens, Olson & Bear, LLP.

(57) ABSTRACT

A fluid dispenser comprises a fluid chamber having two actuators coupled thereto. One of the actuators damps a fluid response of the other. The fluid chamber may comprises a cylindrical capillary, and the actuators may comprise spaced cylindrical piezoelectric elements.

8 Claims, 5 Drawing Sheets

FLUID DISPENSER AND DISPENSING METHODS

TECHNICAL FIELD

The invention pertains to the controlled dispensing of small volumes of fluid. The invention has particularly advantageous application to automated and integrated systems and methods for rapidly identifying chemicals with biological activity in liquid samples, particularly automated screening of low volume samples for new medicines, agrochemicals, or cosmetics

INTRODUCTION

The dispensing of small volumes of fluids is an important aspect of several different technologies, from various printing techniques to chemical screening apparatus for drug discovery. Thus, systems and methods for controllably and accurately dispensing liquid, especially small liquid samples, can benefit a number of different fields. The agrochemical, pharmaceutical, and cosmetic fields all have applications where large numbers of liquid samples containing chemicals are processed. In some instances, the processing of liquid samples, such as in pharmaceutical arts, which usually demands complicated liquid processing for drug discovery, can obtain throughput rates of approximately 10,000 samples per day or greater.

A wide variety of designs for dispensers have been utilized. In some applications, a piezoelectric actuator is coupled to a fluid chamber that contains a nozzle for droplet ejection. When the piezoelectric material is actuated, a droplet of fluid is ejected through the nozzle. Such a system is illustrated in U.S. Pat. No. 4,877,745 to Hayes, et al., which is incorporated herein by reference in its entirety.

This method of droplet ejection includes several complications, however, such as the production of undesired fluid responses to actuation which interfere with efficient droplet ejection. One possible method of damping undesired fluid responses in a piezoelectrically compressed fluid chamber involves placing selected materials inside or around the rearward portion of the fluid chamber that cushion or passively dampen the pressure wave in the chamber. Some of these techniques are described, for example, in U.S. Pat. No. 3,832,579 to Arndt, U.S. Pat. No. 4,233,610 to Fischbeck et al., and U.S. Pat. No. 4,528,579 to Brescia. However, these passive systems are relatively expensive to implement, and may need significant alteration depending on the physical properties of the fluid being dispensed.

Another proposed solution to undesired fluid responses, illustrated in U.S. Pat. No. 4,418,354 to Perduijn (which is hereby incorporated into the present disclosure by reference), involves placing a fluid flow restriction in a portion of the fluid chamber rearward from the nozzle. A dispensing apparatus with a similar functional constriction is commercially available from Packard Instrument Company of Meridan, Conn. as an accessory to the MultiProbe 104. The presence of the restriction, however, produces additional difficulties, such as inhibiting removal of particulate matter that may become inadvertently introduced into the fluid chamber. Once a particle gets inside the fluid chamber, it may become trapped between the small diameter nozzle and small diameter restriction, thereby clogging the device and interfering with the proper operation of the dispenser.

A need therefore exists for efficient droplet dispensing devices which do not suffer from the above mentioned drawbacks.

SUMMARY OF THE INVENTION

The invention is directed to method and apparatus for fluid dispensing. In one embodiment a fluid dispensing apparatus includes a fluid chamber having an opening for droplet dispensing, a first actuator mechanically coupled to and configured to alter the volume of the fluid chamber, and a second actuator mechanically coupled to and configured to alter the volume the fluid chamber. The apparatus may also include a driver connected to actuate the first and second actuators so as to alter the volume of the fluid chamber, whereby a fluid response produced by the first actuator is damped by the second actuator. The actuators may comprise piezoelectric actuators which are actuated substantially simultaneously or sequentially.

Methods of droplet dispensing may comprise altering the volume of a fluid chamber with a first actuator and damping a fluid response to the volume alteration with a second actuator. In one specific embodiment, the altering comprises electrically actuating a first piece of piezoelectric material, and wherein the damping comprises electrically actuating a second piece of piezoelectric material.

DETAILED DESCRIPTION OF THE INVENTION

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Figure 1:
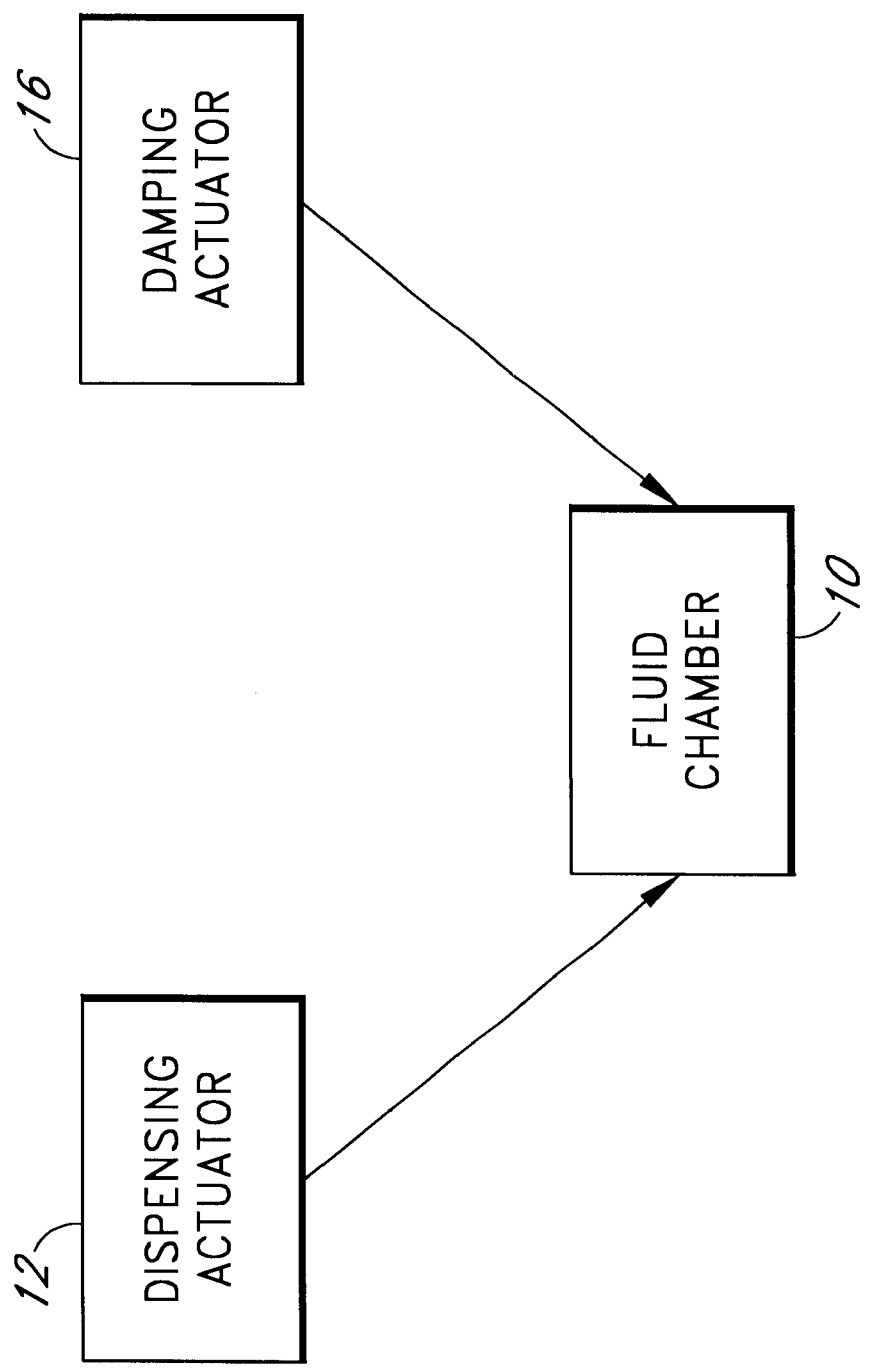
FIG. 1 is a block diagram of a dispensing device in accordance with the invention.

Referring now to FIG. 1, a block diagram representation of a droplet dispensing device according to one embodiment of the invention is shown. The device includes a fluid chamber 10. This fluid chamber 10 includes an opening (not shown in FIG. 1) from which fluid is ejected. The fluid chamber will also generally be connected to a large volume source of solvent (not shown in FIG. 1) for replenishing expelled fluid. The dispensing device may eject fluid received form this fluid source. In many other instances, however, the fluid ejected from the nozzle will have previously been aspirated into the chamber 10 through the nozzle rather than received from a large volume source.

Droplets are dispensed from the fluid chamber by altering the fluid chamber volume with actuators which are mechanically coupled to the fluid chamber. This may be done by compressing the chamber so as to squeeze out a droplet, and then letting the chamber expand to its original volume. This may also be done by first expanding the chamber so as to draw additional fluid from the large volume source, and then letting the chamber contract to its original volume so as to squeeze out a droplet.

In many prior art designs, when the fluid chamber is compressed by actuation, the fluid will not only be forced in a forward direction toward the nozzle, but will also be forced backward away from the nozzle at the same time. This rearwardly directed fluid response hinders the capacity of the nozzle directed fluid response to overcome fluid surface tension at the nozzle. Droplet ejection can be therefore inefficient and may even be impossible.

In the embodiment of FIG. 1, however, the fluid chamber 10 is coupled to two actuators, referred to as a dispensing actuator 12, and a damping actuator 16 (as represented schematically by the arrows pointing toward the fluid chamber 10). These two actuators 12, 16 together provide efficient droplet dispensing without the drawbacks associated with prior art dispensing apparati. In some embodiments, the dispensing actuator 12 may be more closely associated with the ejection nozzle of the fluid chamber than the damping actuator 16, and may thus be more directly associated with droplet ejection. In these embodiments, the damping actuator 16 has the principal function of damping a fluid response to actuation of the dispensing actuator 12. The fluid response damped by the damping actuator 16 may advantageously be a response that otherwise reduces the efficiency of droplet ejection. It will be appreciated by those of skill in the art, however, that the labels "dispensing" and "damping" for the two actuators are not mutually exclusive. In particular, it will be appreciated that both actuators 12 and 16 are involved in the dispensing function and that each may be considered to perform a damping function with regard to a fluid response produced by the other actuator. One beneficial aspect of the dispensing apparatus illustrated in FIG. 1, however, is that fluid responses which inhibit droplet ejection are predominantly damped, thereby increasing the efficiency of droplet ejection in an inexpensive manner which avoids problems with prior art apparatus.

It will be appreciated by those in the art that a wide variety of actuators and methods of coupling actuators to fluid chambers have been devised and are known in the art. In most instances, the actuators used are made of a piezoelectric material which expands, bends, leans, or otherwise deforms in response to an applied voltage. In some cases, the actuators are flexing planar membranes. In others, the actuator undergoes a piston-like motion to eject a droplet. In still other cases, the walls of the fluid chamber are themselves made of a piezoelectric material. It will be appreciated that each individual actuator 12, 16 and its coupling to the fluid chamber 10 may be implemented using any actuation technique which suits the desired dispensing application.

Figure 2:
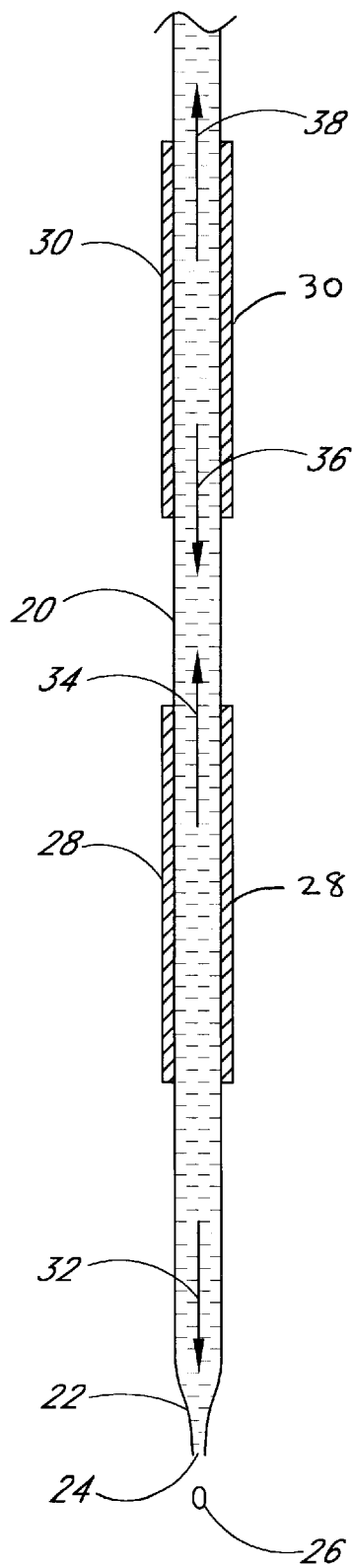
FIG. 2 is a cross section of a cylindrical droplet dispensing device in accordance with the invention.

One specific embodiment of a dispensing apparatus which utilizes the principles discussed with regard to FIG. 1 above is illustrated in cross section in FIG. 2. This embodiment comprises a substantially cylindrical capillary 20 made of any number of suitable materials such as quartz or glass. The capillary 20 has a tapered end 22 which terminates in an opening 24 which forms the nozzle from which droplets of fluid 26 are dispensed.

Surrounding the capillary 20 are two cylindrical piezoelectric actuators 28, 30. One of these actuators 28 is positioned closer to the opening 24 than the other actuator 30. In operation, the lower actuator 28 may be actuated so as to compress the region of the capillary 20 inside the lower actuator 28. When this occurs, pressure waves force fluid both downward toward the nozzle 24 in the direction of the arrow 32 and upward away from the nozzle 24 and toward the second actuator 30. The upper actuator 30 may also be actuated, producing pressure waves which force fluid downward toward the first actuator 28 in the direction of arrow 36 as well as upward out of the second actuator 30 in the direction of arrow 38.

The net effect of the actuation of both actuators 28 and 30 is that the fluid response to the first actuator 28 which is directed upward and away from the nozzle is damped by the presence of the downwardly directed fluid response produced by the second actuator 30. This isolates the lower portion of the capillary 20, prevents significant fluid flow away from the nozzle, and allows the lower actuator 28 to efficiently produce a pressure pulse in the region of the nozzle 24 which can overcome the surface tension of the fluid and eject a droplet 26.

Several advantages to the designs described herein over the prior art are apparent. First, no constriction needs to be present in the capillary 20 in the region upward from the nozzle 24. As described above, a constriction may be designed to function to isolate the lower region of the capillary to enhance the efficiency of droplet ejection, but inhibits the ability to remove trapped particulates from the system. Also, the constriction adds to the cost of manufacturing the capillary. In addition, the "virtual constriction" produced by the second actuator 30 improves dispensing efficiency so that both actuators 28, 30 can be moved farther away from the nozzle 24 and still controllably eject fluid droplets. Moving the actuators further from the nozzle is advantageous because the capillary 20 may extend further down into sample wells during aspiration and fluid dispensing.

In one specific embodiment, the capillary 20 comprises a quartz tube having an approximately 1 mm outer diameter and an approximately 0.82 mm inner diameter, tapering down to a nozzle with a diameter of approximately 70 microns. The actuators 28, 30 comprise approximately 12 mm long cylindrical shells of piezoelectric material such as lead-zirconium-titanate (PZT) having an approximately 1.14 mm inner diameter and a 2.13 mm outer diameter. These dimensions may, of course, vary widely depending on the desired drop volumes. The actuators may be mounted on the capillary 20 such that the lowest extent of the lower actuator 28 is more than 10 mm away from the nozzle 24. In some embodiments, the lowest extent of the lower actuator 28 is more than 20 mm away from the nozzle 24, with approximately 16 mm away having been found suitable in one specific embodiment. The actuators 28, 30 may be separated by anywhere from 0 to 10 or more mm. In one embodiment, approximately 3 mm has been found suitable. They may be held in place on the capillary 20 with a small amount of epoxy or other suitable adhesive.

Figure 3:
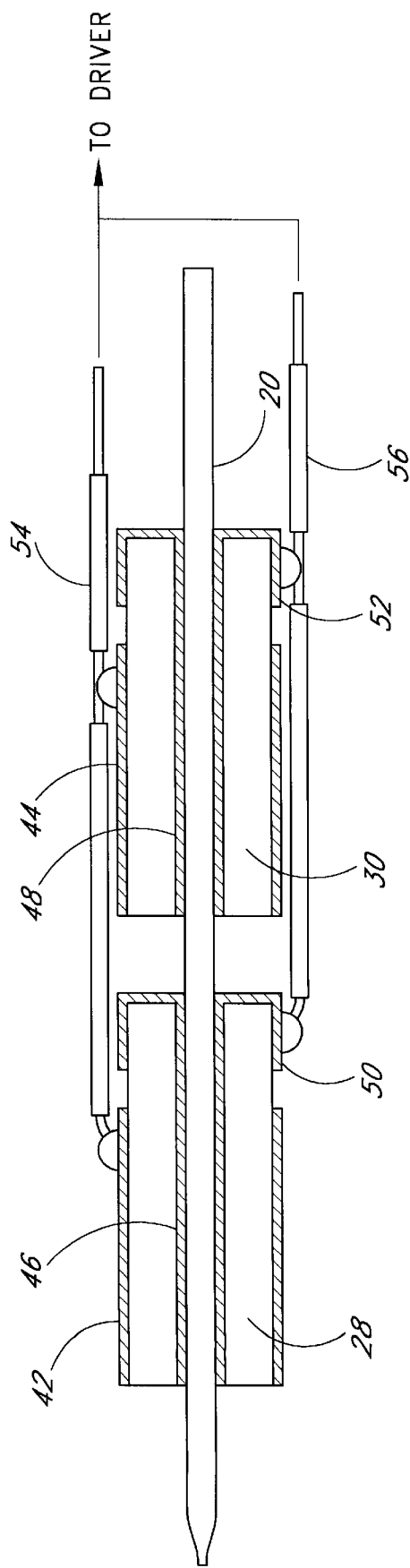
FIG. 3 is a cross section of a cylindrical drop dispensing device illustrating one embodiment of the electrical connection between piezoelectric actuators and a driver circuit.
Figure 4:
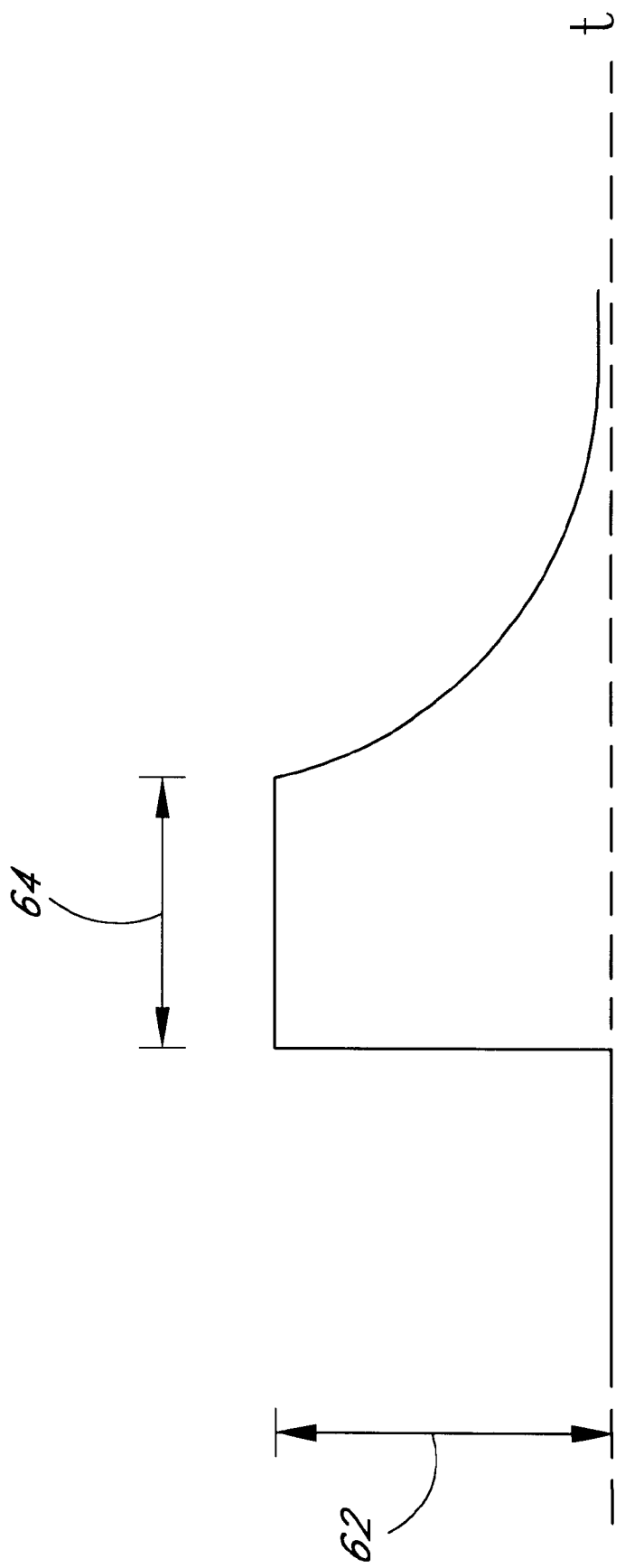
FIG. 4 is a graphical illustration of one embodiment of a voltage waveform suitable for actuating the piezoelectric actuators of FIGS. 2 and 3.

Turning now to FIGS. 3 and 4, actuation of the piezoelectric actuators 28, 30 will be described. As is well known in the art, cylindrical piezoelectric actuators may be provided with two electrodes, one on the inner surface, and one on the outer surface. The material is polarized radially such that the application of a voltage of the correct polarity produces a radial expansion of the material. This expansion may be used to compress a fluid filled capillary such as is illustrated in FIG. 2. In FIG. 3, another cross section is set forth, again showing the piezoelectric actuators 28, 30 which surround the capillary 20.

The actuators 28, 30 are each provided with an outer electrode 42, 44 respectively and an inner electrode 46, 48 respectively. The electrodes may advantageously comprise a nickel plating. For convenient access to the inner electrodes 46, 48, it is common to wrap the inner electrode plating around one end of the actuator to provide electrode portions 50, 52 which are on the outer surface of the actuators 28, 30, but which are electrically connected to the inner electrodes 46, 48. It will be appreciated that in FIG. 3, the actuators 28, 30, and the electrodes 42, 44, 46, and 48 are shown much thicker than in reality for clarity of illustration.

It has been found that simultaneous actuation of both actuators 28, 30 produces the advantageous features of the dual actuator configuration described above. Accordingly, and as illustrated in FIG. 3, the actuators 28, 30 are connected to a driver circuit in parallel. In particular, a first wire 54 is soldered to the outer electrode 42 of the first actuator 28 and the outer electrode 44 of the second actuator 30. In addition, a second wire 56 is soldered to the inner electrode 46 of the first actuator 28 and the inner electrode 48 of the second actuator 30. The solder connections to the inner electrode may advantageously be made to the outer portions 50, 52 of the inner electrodes 46, 48. The wires 54, 56 are connected to a driver circuit which applies a voltage pulse to the electrodes to compress the capillary 20 and eject the droplets as described above in conjunction with FIG. 2.

One embodiment of a voltage waveform which has been found suitable for use with the dispensing device of FIGS. 2 and 3 is illustrated in FIG. 4. The pulse shown is applied such that the positive electrode is on the inner surface of the actuators 28, 30, and the ground electrode is on the outer surface of the actuators 28, 30. The height 62 of the waveform may be approximately 60 to 150 V with a rise time of about 70 microseconds or less. In general, with a faster rise time, the height 62 of the pulse may be reduced while still producing acceptable droplet formation. The duration 64 of the pulse may be from 20 or 30 microseconds up to one millisecond or more. 500 microseconds has been found suitable in one specific embodiment. The pulse is preferably ramped downward somewhat slowly from its peak value to help eliminate multiple droplet ejection with a single pulse. In one embodiment, the voltage drops approximately exponentially to essentially zero in approximately 1 or more milliseconds, with approximately 2 milliseconds having been found suitable in one embodiment. This decay can also be significantly shorter than 1 millisecond while retaining the desired effect Because material and manufacturing variations will affect droplet size and efficiency of ejection, it can be advantageous to separately calibrate each dispensing device such that a known volume of fluid is dispensed with each pulse for each dispensing device produced. This may be done by measuring drop volume as a function of pulse height 62, and subsequently driving the device during use with a pulse having a height determined to produce the selected drop volume.

In reagent dispensing environments, for example, it is usually advantageous to dispense less than approximately 2,000 nanoliters of liquid with each pulse. Preferably, nanoliter dispensers as described herein can dispense less than approximately 500 nanoliters, more preferably less than approximately 100 nanoliters, and most preferably less than approximately 25 nanoliters. Preferred, minimal volumes dispensed are 5 nanoliters, 500 picoliters, 100 picoliters, 10 picoliters. It is understood that dispensers capable of dispensing such minimal volumes are also capable of dispensing greater volumes. The volume dispensed with each pulse will be largely dependent on the pulse height, capillary size, and actuator position. Maximum volumes dispensed are about 10.0 microliters, 1.0 microliters, and 200 nanoliters. In the specific 1 mm outer diameter capillary embodiment described with reference to FIGS. 2, 3, and 4, dispensed volume will typically range from approximately 50 to 400 picoliters. Duty cycle may range from 10 pulses per second to 1000 or more pulses per second, depending on the driving pulse width illustrated in FIG. 4. In one specific embodiment, 100 droplet dispenses per second is utilized.

Alternative actuator driving schemes may also be used in addition to the substantially simultaneous driving described above. For example, it may be desirable to independently drive the piezoelectric actuators 28, 30. They may, for example, be driven sequentially. In these embodiments, the upper actuator 30 may be pulsed slightly ahead of the lower actuator so that the downwardly directed fluid responses add together to enhance the efficiency of droplet formation. This may be especially advantageous when more viscous fluids are being ejected. Different pulse shapes may also be used for the different actuators. Furthermore, configurations having three or more simultaneously or sequentially driven actuators may be utilized.

As mentioned above, the fluid dispensing apparatus described with reference to FIGS. 1 through 3 finds especially advantageous application to high throughput chemical screening apparatus. An example of such an application is presented in FIG. 5. The dispensing apparatus described above may advantageously be incorporated into a sample distribution module in a chemical screening apparatus that can dispense or aspirate large numbers of solutions, usually small volume solutions. In many instances, the sample distribution module will hold large numbers of different stock solutions of chemicals dissolved in aqueous or non-aqueous solvents (e.g., water or dimethylsulfoxide (DMSO)) in addressable chemical wells. To facilitate the rapid transfer of these stock solutions, it is desirable for the sample distribution module to aspirate a stock solution from an addressable well and dispense all or a portion of that solution into an addressable sample well or another addressable well. This sequence of events can be progammably controlled to ensure that the stock solution is aspirated from a pre-selected addressable chemical well and is dispensed into a pre-selected addressable sample well. A chemical screening system with these features is described in co-pending and co-owned PCT Patent Application No. PCT/US98/09526, filed May 14, 1998 and entitled "Systems and Methods for Rapidly Identifying Useful Chemicals in Liquid Samples" by Stylli et al. This screening system may advantageously incorporate the droplet dispensing apparatus described herein. The "Systems and Methods for Rapidly Identifying Useful Chemicals in Liquid Samples" patent application is hereby incorporated by reference in its entirety.

Figure 5:
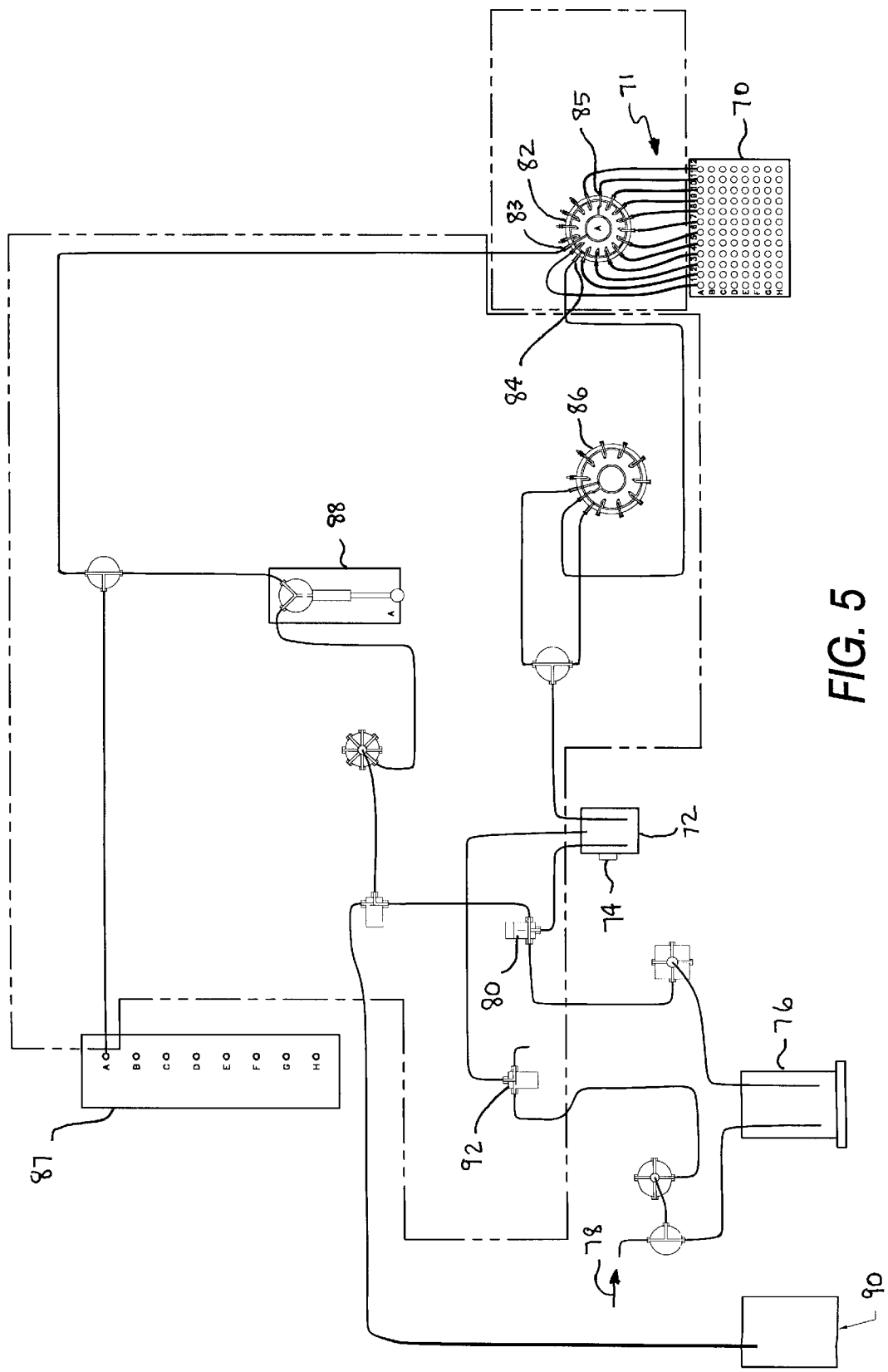
FIG. 5 is a block diagram illustrating a fluid delivery system into which the dispensers of FIGS. 2 and 3 may be advantageously incorporated.

In one embodiment, the system may comprise a plurality of nanoliter dispensers that can individually dispense a predetermined volume. Typically, dispensers are arranged in two-dimension array to handle plates of different well densities (e.g., 96, 384, 864 and 3,456). In FIG. 5, a 96 dispenser array 70 is illustrated, shown as 8 sets of 12 dispensers, with each set being designated by a letter A through H. The dispensers are coupled to a set of feed lines 71. This coupling may be performed in any number of ways well known or devisable by those of skill in the art. In one embodiment, the portion of the dispenser comprising the actuators and wiring illustrated in FIG. 3 is placed in a hollow plastic casing which contains integral terminals for the wires 54, 56, and an integral stainless steel sleeve which has one end that slides snugly over the end of the capillary 20 opposite the nozzle and has another end that extends out of the plastic casing. The case is filled with epoxy potting and cured to secure solder joints between the wires and the terminals, and to seal the coupling between the quartz capillary and the stainless steel tube. The feed lines 71 may then be secured over the stainless steel tubes to provide a sealed fluid coupling between each dispenser and a source of solvent. Furthermore, the terminals provided with the plastic casing may be connected to a driver circuit provided as part of the screening so as to provide electrical actuation to the piezoelectric elements inside.

The dispensers receive solvent such as water or DMSO from a vented reservoir 72. The vented reservoir includes a liquid level sensor 74. The height of the solvent in the reservoir 72 is maintained at a level of approximately 12 to 25 mm below the level of the nozzles of the dispensers in the array 70. This maintains a slight negative pressure in the capillary, and results in an advantageous slightly inwardly directed meniscus in the solvent at the nozzle of each dispenser.

The fluid level in the vented reservoir 72 is maintained by periodic refilling from a large solvent reservoir 76 which is pressurized by, for example, a source of compressed air 78 regulated to 5 psi. If the level sensor 74 senses too low a level of solvent in the vented reservoir 72, a valve 80 will route a portion of the pressurized solvent to the vented reservoir 72.

Each dispenser in a set of 12 is connected via its associated feed line 71 to a port on a commercially available dispenser valve 82. This valve 82 includes a selected outlet 83 and a common outlet 84. The valve 82 is configured to provide a fluid coupling between the selected outlet 83 and a user selected port, while connecting all other ports to the common outlet 84. In FIG. 5, port 85 is "selected", and the remainder are connected to the "common". The common outlet 84 of the dispenser valve 82 is coupled to the vented solvent reservoir 72 through a second valve 86. In this embodiment, the 96 dispensers in the array 70 are fed from 8 separate 16 port dispenser valves, with each dispenser valve coupled to 12 dispensers. Ports 13–16 of the dispenser valves 82 in this embodiment are plugged off. The common outlet of each of the 8 dispenser valves is coupled to one of the ports of the 10 port second valve 86. The selected outlet of each of the eight dispenser valves is connected to a pressure sensor 87 and to respective negative pressure devices 88. The eight negative pressure devices may advantageously comprise syringe pumps.

As mentioned above, the apparatus preferably will both aspirate reagent up into the capillaries, and dispense reagent from the capillaries. Aspiration of 96 samples may be performed by first selecting port 1 with each dispenser valve 82. With the dispenser tips placed in the desired sample wells, a volume of fluid is drawn into the eight capillaries connected to a port 1 of each dispenser valve using the eight syringe pumps 88. Each syringe pump 88 outlet is then switched toward a waste container 90, and the solvent taken up into the syringe pumps 88 during aspiration is deposited there.

Next, port 2 is selected with each dispenser valve 82. With the dispenser tips still in the desired sample wells, a volume of fluid is drawn into the next eight capillaries using the syringe pumps 88, and the solvent taken up by the syringe pumps 88 during aspiration is expelled into a waste container 90. This process is repeated for ports 3–12 of the dispenser valves.

To dispense the 96 aspirated samples, the dispenser valves 82 are set to select port 13. This connects all 12 ports 1–12 to the vented reservoir 72. With the pressure in the capillaries thus equilibrated to the pressure in the vented reservoir 72, the actuators are pulsed as described above, and 96 volumes of fluid are simultaneously dispensed.

A forward flush process may be performed by sealing and pressurizing the vented reservoir 72. Pressurization may be performed by venting the solvent container 72 through a valve 92 which is coupled to both the ambient atmosphere and to the 5 psi compressed air source 78. During this forward flush procedure, if the all of the dispenser valves 82 are configured to select port 13, all 96 dispensers will be coupled to the previously vented (but now pressurized) solvent reservoir 72. A reverse flush process may be performed by repeating the aspiration technique described above a desired number of times.

All publications and patent documents cited herein are hereby incorporated by reference to the same extent as if they had been individually incorporated by reference.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. An apparatus for dispensing droplets of fluid comprising:
   a fluid chamber having an opening therein for droplet dispensing and having no permanent constriction interfering with flushing of particulate matter from the fluid chamber;
   a first actuator mechanically coupled to said fluid chamber and configured to alter the volume thereof;
   a second actuator mechanically coupled to said fluid chamber and configured to alter the volume thereof, wherein said second actuator is further away from said opening than said first actuator; and
   a driver connected to actuate said first and said second actuators with simultaneous and identical voltage pulses so as to dispense fluid droplets from said fluid chamber.

2. The apparatus of claim 1, wherein said first and said second actuators comprise piezoelectric material.

3. The apparatus of claim 2, wherein said first and said second piezoelectric actuators comprise substantially cylindrical piezoelectric actuators which substantially surround said fluid chamber.

4. The apparatus of claim 1, wherein said fluid chamber comprises a quartz capillary.

5. A chemical screening apparatus comprising:
   a array of reagent dispensers configured to dispense reagents into an array of wells in a multi-well plate, wherein each of said reagent dispensers comprises:
   a substantially cylindrical capillary having a nozzle at one end thereof; and
   at least two substantially cylindrical piezoelectric transducers surrounding said capillary so as to eject said reagent from said capillary through said nozzle, wherein said transducers are all positioned at least about 10 mm away from said nozzle.

6. The reagent dispenser of claim 5, additionally comprising a plurality of negative pressure devices in fluid communication with each said capillary so as to aspirate reagent into said capillary through said nozzle.

7. The reagent dispenser of claim 6, wherein said negative pressure devices comprise syringe pumps.

8. The chemical screening apparatus of claim 5, additionally comprising a voltage source for driving said transducers, wherein said voltage source is connected in parallel to said transducers and drives said transducers with the same voltage waveform at the same time.

\* \* \* \* \*